United States Patent
Ellrich et al.

(10) Patent No.: US 8,940,950 B2
(45) Date of Patent: Jan. 27, 2015

(54) METHOD AND APPARATUS FOR OBTAINING AROMATICS FROM DIVERSE FEEDSTOCK

(75) Inventors: Justin M. Ellrich, Overland Park, NJ (US); Robert D. Strack, Houston, TX (US); John W. Rebeck, Katy, TX (US); Allen S. Gawlik, Houston, TX (US); Larry L. Iaccino, Seabrook, TX (US); Glenn C. Wood, Houston, TX (US); Stephen H. Brown, Annandale, NJ (US); Timothy Paul Bender, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 247 days.

(21) Appl. No.: 13/303,855

(22) Filed: Nov. 23, 2011

(65) Prior Publication Data

US 2012/0149958 A1    Jun. 14, 2012

Related U.S. Application Data

(60) Provisional application No. 61/421,917, filed on Dec. 10, 2010.

(51) Int. Cl.
| | |
|---|---|
| C07C 2/66 | (2006.01) |
| C07C 6/12 | (2006.01) |
| C07C 4/14 | (2006.01) |
| C07C 2/86 | (2006.01) |
| C07C 5/27 | (2006.01) |
| C10G 55/04 | (2006.01) |

(Continued)

(52) U.S. Cl.
CPC .............. *C07C 2/864* (2013.01); *C07C 5/2729* (2013.01); *C10G 55/04* (2013.01); *C10G 55/06* (2013.01); *C10G 57/005* (2013.01); *C07C 5/2767* (2013.01); *C10G 2400/30* (2013.01); *B01J 2219/00006* (2013.01)

USPC ........... 585/319; 585/321; 585/322; 585/323; 208/50; 208/51; 208/53; 208/58; 208/62; 208/66; 208/67; 208/69; 208/70

(58) Field of Classification Search
USPC ........ 585/319, 321, 322, 323; 208/50, 51, 53, 208/58, 62, 66, 67, 69, 70
See application file for complete search history.

(56) References Cited

U.S. PATENT DOCUMENTS

| | | | |
|---|---|---|---|
| 4,053,388 A | 10/1977 | Bailey | |
| 4,058,450 A * | 11/1977 | Le Page et al. | ................. 208/66 |

(Continued)

FOREIGN PATENT DOCUMENTS

| | | |
|---|---|---|
| WO | WO 97/45387 | 12/1997 |
| WO | 02/44306 | 6/2002 |

(Continued)

*Primary Examiner* — Thuan D Dang
(74) *Attorney, Agent, or Firm* — Andrew B. Griffis

(57) ABSTRACT

The process relates to the use of any naphtha-range stream containing a portion of C8+ aromatics combined with benzene, toluene, and other non-aromatics in the same boiling range to produce toluene. By feeding the A8+ containing stream to a dealkylation/transalkylation/cracking reactor to increase the concentration of toluene in the stream, a more suitable feedstock for the methylation reaction can be produced. This stream can be obtained from a variety of sources, including the pygas stream from a steam cracker, "cat naphtha" from a fluid catalytic cracker, or the heavier portion of reformate.

5 Claims, 6 Drawing Sheets

(51) Int. Cl.
*C10G 55/06* (2006.01)
*C10G 57/00* (2006.01)

(56) References Cited

U.S. PATENT DOCUMENTS

| | | | |
|---|---|---|---|
| 5,043,502 A * | 8/1991 | Martindale et al. | 585/323 |
| 7,176,339 B2 | 2/2007 | Iaccino et al. | |
| 7,179,434 B1 | 2/2007 | Maher et al. | |
| 7,297,831 B2 | 11/2007 | Lee et al. | |
| 7,301,063 B2 | 11/2007 | Choi et al. | |
| 7,563,358 B2 | 7/2009 | Stavens et al. | |
| 7,578,929 B2 | 8/2009 | Stell et al. | |
| 7,629,498 B2 | 12/2009 | Brown et al. | |

FOREIGN PATENT DOCUMENTS

| | | |
|---|---|---|
| WO | WO 2004/005432 | 1/2004 |
| WO | WO 2006/068800 | 6/2006 |
| WO | WO 2010/138504 | 12/2010 |

* cited by examiner

METHOD AND APPARATUS FOR OBTAINING AROMATICS FROM DIVERSE FEEDSTOCK

CROSS REFERENCE TO RELATED APPLICATIONS

This application claims priority to U.S. Provisional Patent Application No. 61/421,917, filed Dec. 10, 2010, which is herein incorporated by reference in its entirety.

FIELD OF THE INVENTION

The invention relates to a process for obtaining purified aromatic hydrocarbons from diverse feedstocks, more particularly a process for the production of paraxylene (PX) from naphtha feedstocks, and also to a system for the practice thereof.

BACKGROUND OF THE INVENTION

Xylene isomers find wide and varied applications. They are especially valuable as intermediates in chemical syntheses. By way of example, paraxylene (PX) is a feedstock for terephthalic acid, which finds use in the manufacture of synthetic fibers and bottle plastic, metaxylene (MX) is used in the manufacture of dyes, and orthoxylene (OX) is used as a feedstock for phthalic anhydride, which finds use in the manufacture of plasticizers. PX is currently the most valuable of the xylene isomers and although patents related to obtaining (e.g., producing or purifying) PX are too numerous to mention, there is still intensive research in the area.

There are many possible feeds currently used to obtain PX. The majority of paraxylene produced today comes from catalytic reforming, well known in the art, which is primarily fed by naphtha feedstocks. The effluent of the reforming process, known as reformate, is rich in aromatics, particularly toluene and mixed xylenes, and is used as feedstock to aromatics plants. Processes exist to increase the yield of paraxylene over the equilibrium mixture in reformate. These include disproportionation of purified toluene selective methylation of benzene and/or toluene, among others. Other sources described below are also possible feeds to paraxylene production processes.

Steam cracking, or pyrolysis, is the preferred method of producing light olefins (ethylene, propylene, and butenes) from hydrocarbon feedstock. Pyrolysis involves heating of the hydrocarbon feedstock to sufficient temperature for thermal cracking of the molecules to the preferred olefinic products. Also produced in this process is a fraction termed pyrolysis gasoline, steam cracked naphtha (SCN) or pygas, that comprises molecules from C6 to C10+ and is rich in aromatics, particularly benzene and toluene as well as C8, C9 and C10+ aromatics.

Catalytic cracking, or fluid catalytic cracking (FCC), is another well-known process that produces fuels, light olefins, and a similar C6 to C10+ aromatic rich stream, known as "cat naphtha."

It is known to produce xylenes by the methylation of toluene, for instance methylation of toluene over a catalyst using methanol. U.S. Pat. No. 7,629,498 discloses a process for (a) contacting a pygas feedstock and methylating agent with a catalyst under reaction conditions to produce a product having paraxylenes, wherein the product has higher paraxylene content than the paraxylene content of the feedstock; and (b) separating the paraxylene from the product of step (a). This patent describes steam cracking one or more crude fractions, separating the products into light olefins and pygas, methylating the C8– fraction to form a paraxylene rich product, recovering said paraxylene, and co-recovering light olefins from the PX-rich effluent. This process also mentions the flexibility to extract the aromatics portion from paraffins, naphthenes, and heavy mono- and di-olefins, which cause deactivation and aging of methylation catalysts, to give a purer aromatic feedstock to the reactor.

U.S. Pat. No. 7,301,063 discloses a process to co-produce an aromatic hydrocarbon mixture and liquefied petroleum gas (LPG) from pyrolysis gasoline. The resulting LPG can then be recycled back to the steam cracker which produced the pygas. This process involves contacting the separated pyrolysis gasoline stream, another hydrocarbon feedstock, and hydrogen into at least one reaction area with catalyst, thus converting the mixture into an aromatic fraction rich in benzene, toluene, and xylenes through dealkylation/transalkylation reactions and a fraction rich in LPG through a hydrocracking reaction.

U.S. Pat. No. 7,297,831 discloses a process of preparing aromatic hydrocarbons and liquefied petroleum gas (LPG) from a hydrocarbon mixture, in which a non-aromatic compound in the hydrocarbon feedstock mixture is converted into a gaseous material having a large amount of LPG through hydrocracking, and an aromatic compound therein is converted into an oil component having a large amount of benzene, toluene, and xylene (BTX) through dealkylation and transalkylation.

WO 02/44306 discloses a process for producing aromatic hydrocarbon compounds and liquefied petroleum gas (LPG) from a hydrocarbon feedstock. Aromatic components in the feedstock are converted to BTX-enriched components of liquid phase through hydrodealkylation and/or transalkylation, and non-aromatic components are converted to LPG-enriched gaseous materials through hydrocracking.

U.S. Pat. No. 7,578,929 describes cracking heavy hydrocarbon feedstock containing non-volatile hydrocarbons including mixing the feedstock with a fluid and/or primary dilution steam stream according to a preselected operating parameter of the process.

U.S. Pat. No. 7,563,358 teaches a hydrocarbon conversion process for producing an aromatics product containing one or more BTX species from precursors of the one or more BTX species.

See also U.S. Pat. No. 7,176,339.

The above processes have not been integrated into a single system that offers significant advantages including higher petrochemical yields and lower energy consumption over operation of the processes separately, and wherein benzene and toluene are made "on purpose" from a refinery feedstream in order to provide a more advantageous feed to an alkylation reactor to selectively produce para-xylene (PX).

The present inventors have surprisingly discovered an advantageous system and process, including, in embodiments, the combination of various streams and utilities which provide significant advantages over prior systems.

SUMMARY OF THE INVENTION

The invention is directed to a process and apparatus or system for obtaining C6 to C8 aromatics, particularly paraxylene, from naphtha-range feedstreams, including one or more steps of methylating benzene and/or toluene with methanol, wherein a C6-C10+ aromatic hydrocarbon feedstream, such as a naphtha feedstream is subjected to one or more of dealkylation, transalkylation, and cracking, to increase the benzene and/or toluene content thereof, and then methylated, preferably with methanol with an appropriate catalyst under suitable conditions to selectively produce para-xylene.

In embodiments the naphtha-range feedstreams are selected from one or more of pygas from a steam cracker, cat naphtha from a fluid catalytic cracker, coker naphtha from a coker, hydrocracked naphtha from a hydrocracker, or a reformate stream from a reformer.

In embodiments the process includes one or more steps selected from dealkylation, transalkylation, and cracking.

It is an object of the invention to provide a process allowing for integration of systems to provide heretofore unobtainable efficiencies in the production of paraxylene.

It is further an object of the invention to increase the benzene and/or toluene content of a refinery feedstream prior to methylation.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
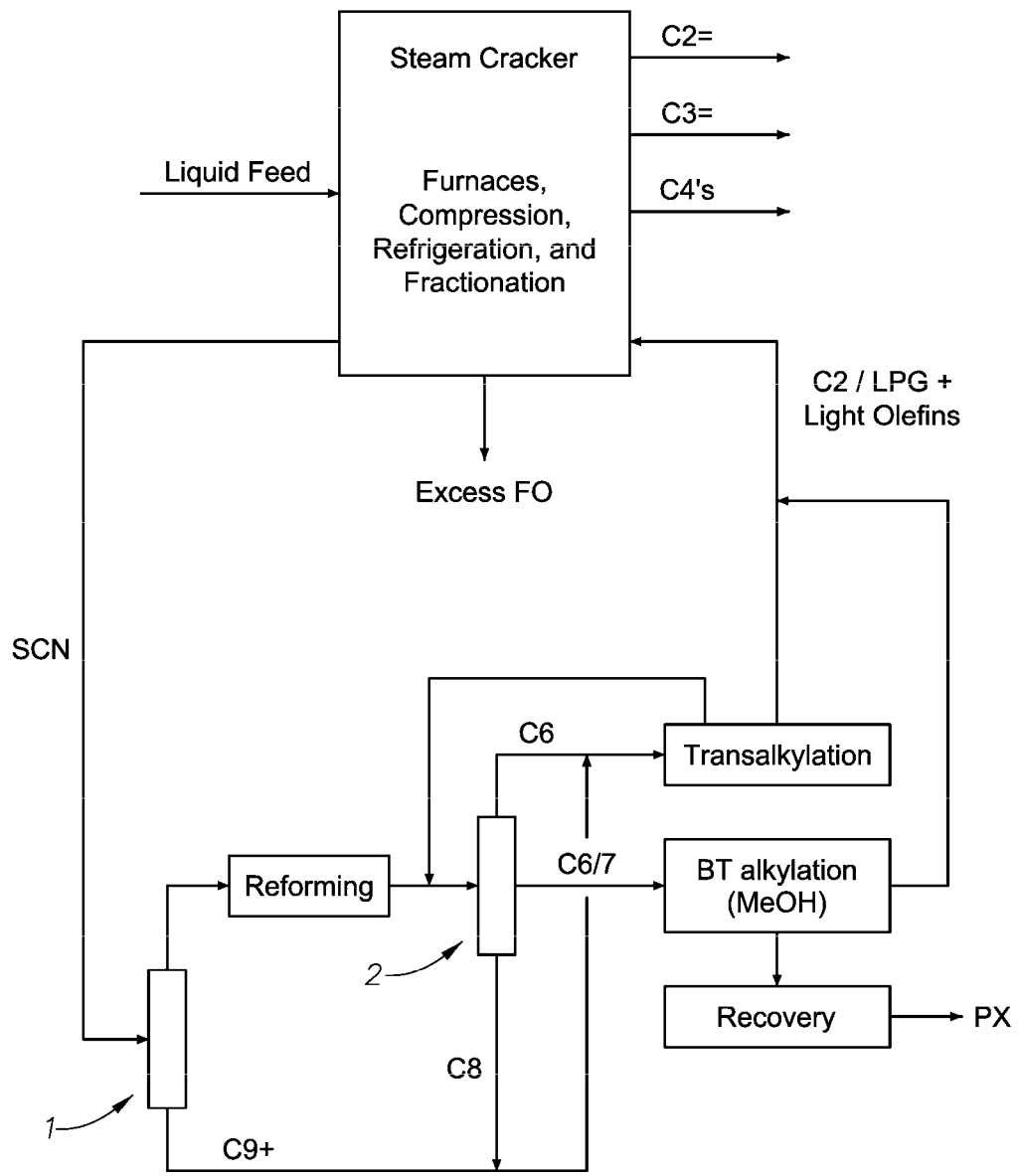
FIGS. 1-6 illustrate embodiments of an integrated system according to the present invention

According to the invention, in embodiments, there is a process for manufacturing para-xylene using a feedstream comprising naphtha which is processed to increase the benzene and/or toluene content thereof prior to contact with a methylating agent in the presence of a catalyst selective for the production of para-xylene, and a system adapted therefor.

In embodiments, the process comprises: (a) dealkylation and/or transalkylation and/or cracking (D/T/C) of the naphtha stream over a catalyst at reaction conditions to enrich the benzene and/or toluene concentration and produce a light paraffin by-product; (b) addition of a methylating agent to all or part of at least the benzene/toluene portion of the product from step (a) and contacting the mixture with catalyst selective for para-xylene production at reaction conditions to produce para-xylene and light olefin or light paraffin by-products; (c) recovery of purified para-xylene from step (b) as the product of the manufacturing process.

In some embodiments, all or part of the naphtha feedstock may be supplied to a reformer, steam cracker, or catalytic cracker prior to the dealkylation/transalkylation/cracking ("D/T/C") reactor. In preferred embodiments, the reforming step may include conventional reforming, single-bed naphthene aromatization, or HDS reforming HDS reforming is discussed, for instance, in U.S. Pat. No. 7,563,358. Steam crackers and catalytic crackers (cat crackers) are per se also well-known in the art.

In some embodiments, all or part of the naphtha feedstock may undergo isomerization to convert ethylbenzene to xylenes.

In some embodiments, all or part of the naphtha feedstock may be subjected to a hydrotreating process to remove a portion or all of the di-olefins, or moreover a portion or all of the mono-olefins.

In some embodiments, all or part of the naphtha feedstock and/or product from step (a) may be subjected to a de-hexane process where C6 paraffins are separated from C6 naphthenes and benzene.

In some embodiments, all or part of the naphtha feedstock and/or product from step (a) may be subjected to a de-benzene process to remove at least a portion of the benzene in the feedstock. In preferred embodiments, the separated benzene can then go through an extraction process to be sold, or it can be recycled to another step in the aromatics circuit.

In some embodiments, all or part of the naphtha feedstock may be subjected to fractionation to remove toluene prior to the dealkylation/transalkylation/cracking reactor.

In some embodiments, all or part of the naphtha feedstock may be subjected to any combination of a hydrotreating process, reforming process, isomerization process, de-hexane and/or de-benzene and/or de-toluene process, and/or optionally with an extraction step to remove at least a portion non-aromatics (naphthenes and paraffins) prior to contacting the dealkylation/transalkylation/cracking reaction zone and/or the methylation reaction zone.

According to the present invention, particularly advantageous sources of naphtha feedstock include pygas, cat naptha, coker naphtha, hydrocracker naphtha, and reformate. Pygas as used herein means a C6-C10+ cut of the pyrolysis effluent from a steam cracking furnace.

Additionally, the light paraffins and light olefins produced in the above processes can be transferred to the steam cracking furnaces and/or recovery section to enhance the yield of light olefins.

Typically, the pyrolysis gasoline contains from about 15 to about 65 wt % benzene, and from about 5 to about 35 wt % toluene, and contains at least 1 wt % non-aromatics but can be up to 50 wt % non-aromatics depending on composition of feedstock to the steam cracker, intensity of the pyrolysis reaction, and separation and processing scheme for the pygas stream. Generally, as the intensity of the pyrolysis reaction increases, which can be noted by the rising outlet temperature of the reactor or by the changing of the ratio of two products, such as propylene and methane, more aromatics will be present in the effluent.

Also, as composition of the feedstock to the pyrolysis furnace changes, the yield of aromatics in the pygas will also change. Higher molecular weight feedstocks tend to produce more aromatics though they may be more dilute. Lower hydrogen content feedstocks also tend to produce more aromatics. Naphthas and gasoils are conventional feedstocks to steam crackers, including virgin and hydrotreated streams. Resid-containing feeds (considerable portion of 1050° F.+) can be processed by first passing through the convection section of the steam cracking furnace, then passing to a vapor/liquid separating drum, which can optionally be integrated with the pyrolysis furnace, to drop out the heaviest fraction.

Other potential feed sources are "Cat naphtha," which is produced from a fluid catalytic cracker; and reformate, which is a common feedstock to traditional aromatics plants.

The invention may be better understood by reference to the accompanying figures, which illustrates an embodiment of the present invention.

FIG. 1 is a schematic showing a system for obtaining paraxylene (PX) wherein a feedstream comprising C6-C10+ aromatic hydrocarbons, such as conveniently provided by naphtha, is provided to a steam cracker to yield steam cracked naphtha (SCN), light olefins, and fuel oil (FO). Details of the steam cracker system, including furnaces, compressors, refrigeration, fractionator, and the like, required to provide the various streams shown are per se known and within the skill of the ordinary artisan to design. SCN is passed to a first fractionator 1 to provide C9+ hydrocarbons as a bottoms product and lighter materials, including xylene isomers, ethyl benzene, and C7− aromatics are taken overhead. The overhead is sent to a reformer to provide feed to a second fractionator 2, while the bottoms product yields C9+ aromatics. The second fractionator 2 yields an overhead comprising benzene, a side stream comprising toluene and some benzene, and a bottoms product comprising xylenes. As shown in the embodiment of FIG. 1, the bottoms product of the second fractionator 2 and first fractionator 1 are merged and this mixture, comprising C8+ aromatics, is then mixed with the overheads of the second fractionator 2 and provided to a reactor for at least one of dealkylation, transalkylation, or cracking ("D/T/C") comprising the appropriate catalyst system ("D/T/C catalyst system"), which can be selected by one of skill in the art in possession of the present disclosure without undue experimentation. In the embodiment according to FIG. 1, a transalkylation reactor is shown as the D/T/C reactor. The C6+ product from the D/T/C reactor is sent to the fractionator 2 while the C5– product is recycled to the steam cracker as feed (line indicated at "C2/LPG+light olefins). The side stream from the second fractionator, 2, comprising toluene and some benzene, is sent to a benzene and/or toluene alkylation reactor ("BT alkylation (MeOH)"), to be converted to xylenes, preferably with methanol (MeOH) which is then sent to a PX recovery unit, per se known in the art (e.g., crystallizer or Parex™ adsorptive separation unit), to yield a PX rich stream and a PX-depleted stream (the latter not shown). The PX depleted stream may be recycled to the D/T/C reactor and/or said stream can be isomerized to equilibrium xylenes by methods per se well-known in the art and recycled to the PX recovery unit. C5– products (which may include ethylene and propylene) leave the alkylation reactor and, in the present embodiment, are merged with the C5– product of the transalkylation reactor and returned to the steam cracker for recovery and/or upgrading.

Figure 2:
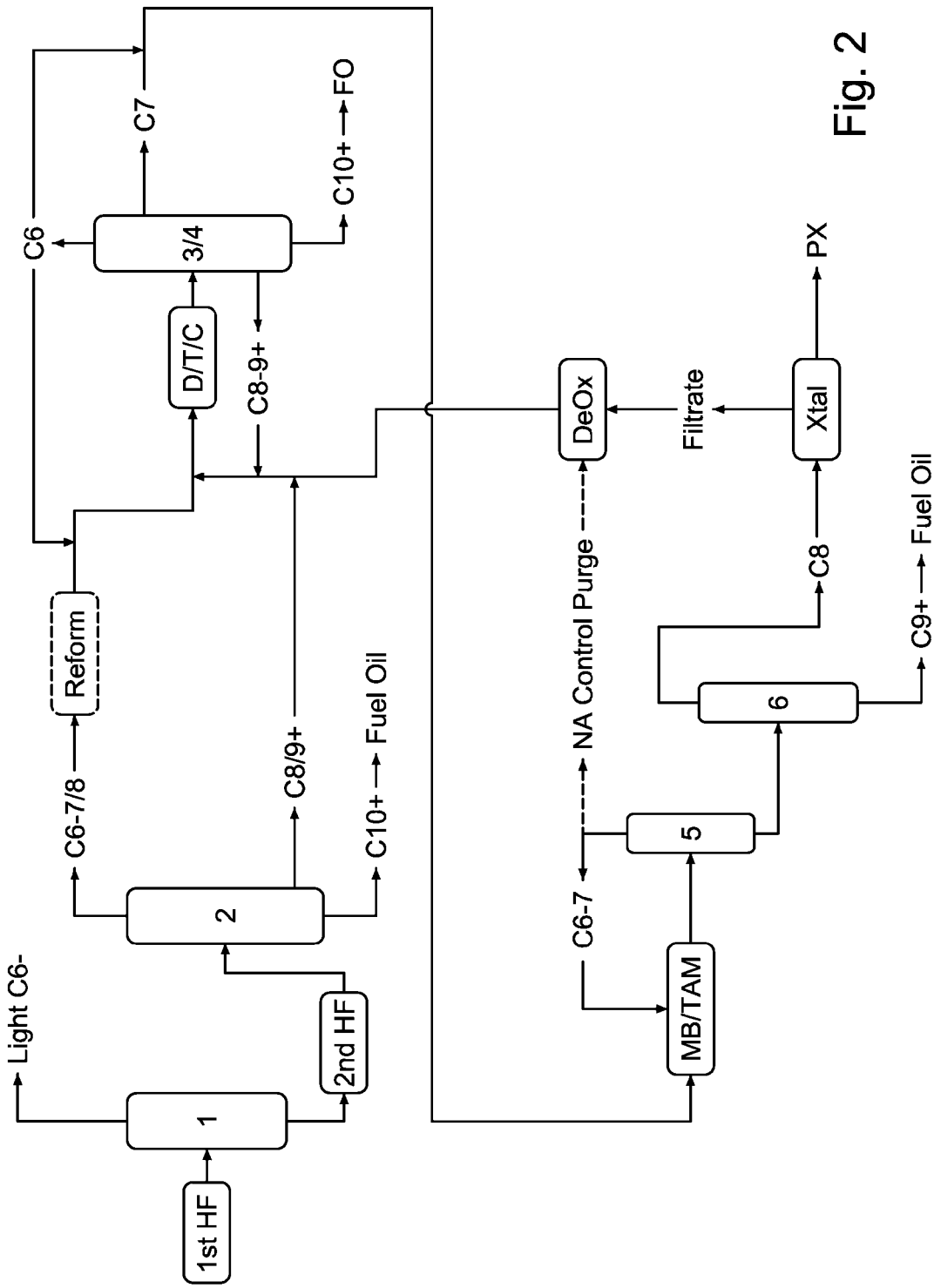

Another embodiment of the present invention is illustrated in FIG. 2. A stream comprising naptha is first treated in a first stage hydrofiner (1st HF in FIG. 2) to take out dienes and styrenes and then to fractionator 1. The light C6– overheads may be further processed by methods per se know in the art and the bottoms product comprising C6+ aromatic hydrocarbons is sent to a second stage hydrofiner (2nd HF) to reduce the olefins. The product stream is then fractionated in fractionator 2 to provide three cuts, which include a C10+ bottoms which may find disposition as Fuel Oil, a side stream comprising mostly C9+ with some C8, the side stream ultimately being sent to the D/T/C reactor (shown in FIG. 2 being joined with several other streams to be discussed), and a C6 to C7 overhead, comprising some C8, which is sent to a reformer where at least a portion of the naphthenes and/or paraffins are converted to aromatics. Alternatively (not shown) the stream may be sent to an extraction unit where the aromatics are extracted from the non-aromatics with the aromatic portion being sent to the D/T/C reactor and the non-aromatic portion being routed to another disposition which may include steam cracker feed and/or gasoline blending.

As shown in FIG. 2, the side stream from fractionator 2 and the product of the reformer are merged and sent the to D/T/C reactor where the combined stream, comprising C6-C9+ aromatic hydrocarbons is contacted with at least one catalyst and under suitable conditions to increase the benzene and/or toluene content of the stream. As shown in FIG. 2, the product of the D/T/C reactor may then be fractionated in one or optionally two fractionators ("3/4" in FIG. 2) and separated into various constituent parts, such as, in this embodiment, a C6 stream, a C7 stream, a C8-C9+ stream, and a C10+ stream. The C6 and C8-C9+ streams may be recycled to the D/T/C reactor, as shown in FIG. 2, the C10+ bottoms product can find various dispositions such as Fuel Oil (FO), and the C7 stream, optionally merged with all or a portion of the C6 stream, is sent to the alkylation reactor (MB/TAM) to be alkylated preferably with methanol to produce, selectively, para-xylene. The lighter products from the alkylation reactor (C5– stream which may contain ethylene and propylene) is not shown but may be routed to a disposition for olefins recovery, steam cracker feed, and/or fuel use. The C6+ product of the alkylation reactor is then fractionated in column 5, with the overhead lighter products being recycled to the alkylation reactor (optional purge to reduce accumulation of non-aromatics is shown by a dotted line) and the bottoms product being sent to a second fractionator 6, where the heavies are separated, shown in the figure as bottoms C9+ with a disposition as fuel oil (FO), and the xylenes being separated in the device indicated by "Xtal", which is preferably a recrystallizer as indicated in the embodiment of FIG. 2, or Parex™ adsorptive separation unit, or some other system, e.g., membrane, xylenes loop, and the like. The raffinate or filtrate from the crystallizer, is preferably sent to a deoxygenator, since oxygen-containing impurities may be present and such impurities may have deleterious effects on downstream operations. After removal of oxygen-containing impurities, the para-xylene depleted stream is recycled back to the D/T/C reactor.

Figure 3:
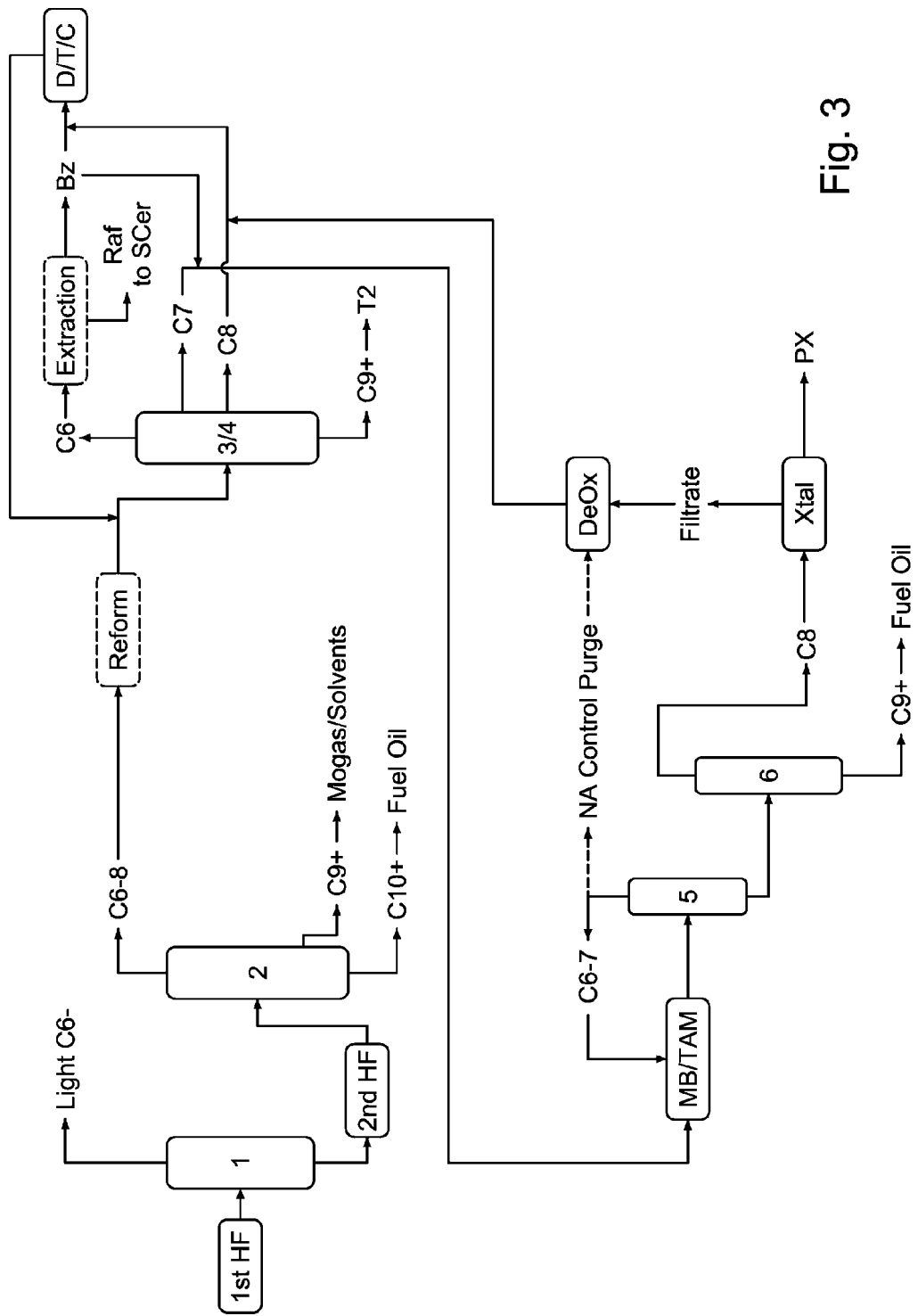

FIG. 3 illustrates yet another embodiment of the present invention. The embodiment is similar to that shown in FIG. 2, except that the process at fractionator 2 is modified to take a C6-C8 overheads to the reformer. The product of the reformer may then be sent to one or more fractionators (as indicated by the one or more columns "3/4" to separate the reformate into four streams, a C6, a C7, a C8, and a C9+ stream. The C9+ stream is returned to fractionator 2 ("T2"). The C7 stream is sent directly to the alkylation reactor ("MB/TAM"), to be discussed below. The C8 stream is sent directly to the D/T/C reactor, merging with the stream from the Extraction unit. The Extraction unit is one of the key differences between FIG. 3 and FIGS. 1 and 2. The extraction unit, per se known in the art, may be any unit or system that extracts aromatic species from non-aromatic species, e.g., liquid-liquid extraction system or extractive distillation unit, both per se known in the art. The extraction unit is advantageously placed upstream of the D/T/C unit or system, preferably as shown in FIG. 3. In another preferred embodiment, not shown, the extraction unit may be placed after the second hydrofinisher in FIG. 2, thus providing a liquid feed substantially free of non-aromatics.

The extraction unit as shown in FIG. 3 provides, from the C6 feedstream overhead of fractionator(s) 3/4, a benzene cut and a raffinate comprising non-aromatics. All or a portion of the benzene may merge with the toluene (C7) cut from the aforementioned fractionator(s) and/or all or a portion of the benzene is provided, optionally with the C8 cut from fractionator(s) 3/4, to the D/T/C reactor, wherein the benzene and/or toluene content is increased. The resultant product is recycled back to the 3/4 fractionator(s) Raffinate from the extraction can be sent to a steam cracker (SCer in FIG. 3 and also FIGS. 4 through 6, discussed below) to increase light olefin yields or used as a blend component for producing gasoline.

Figure 4:
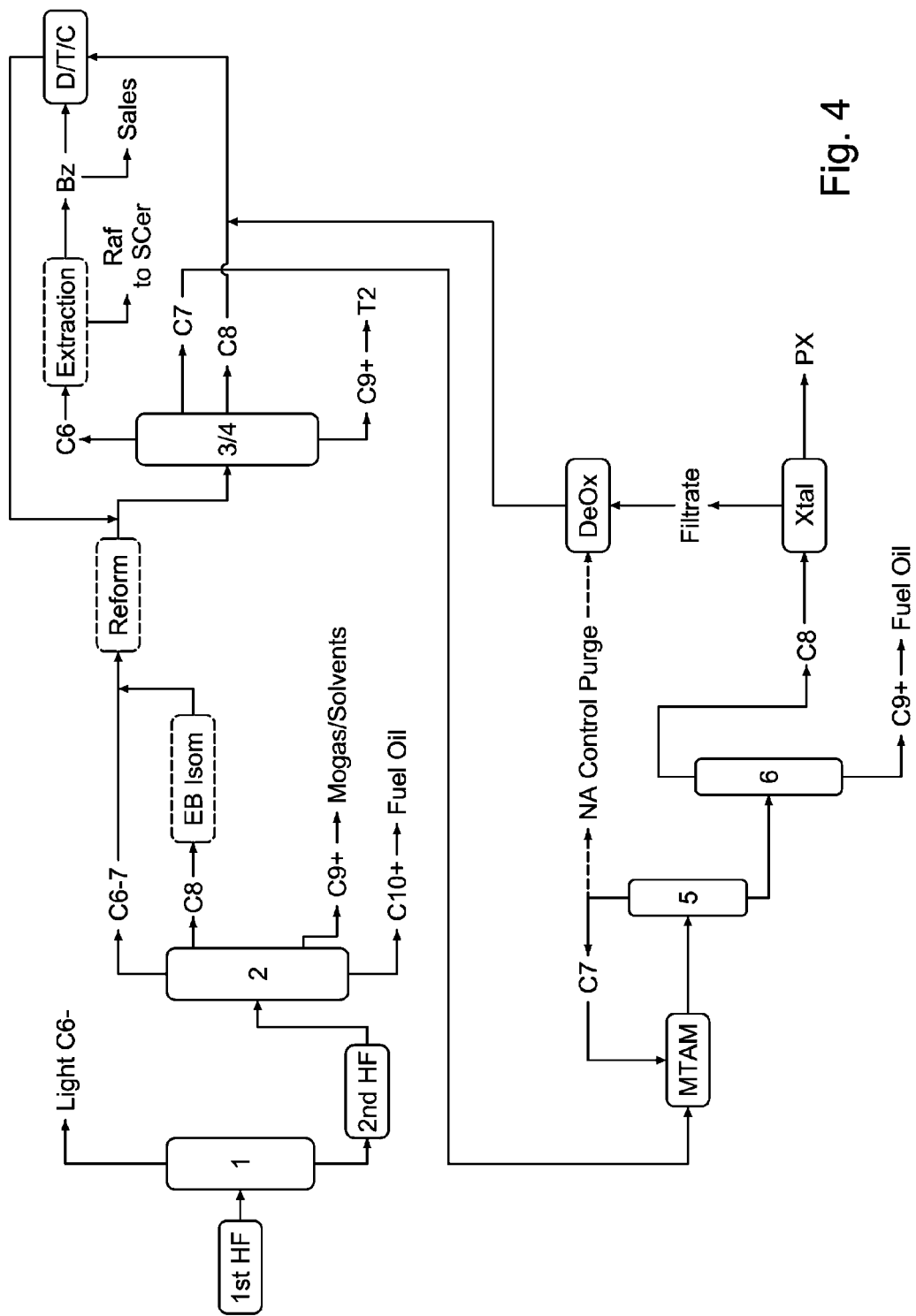

FIG. 4 illustrates still another embodiment of the present invention. In FIG. 4, the process operates substantially as in FIG. 3, the key distinction being fractionator 2, which is operated under conditions sufficient to provide for a C8 side stream, including ethyl benzene (EB), which is then processed through EB Isomerization unit to convert EB to mixed xylenes, also per se known in the art. FIG. 4 also illustrates another possible fate of the benzene produced from the extraction unit, which is disposition of benzene as to sales disposition and the like.

One of the advantages of the present invention as illustrated in FIGS. 2-6 is the use of the recrystallizer downstream of fractionator 6. If the p-xylene content of the C8 stream is >80%, only propylene-level refrigeration is required for the crystallizer, rather than ethylene level refrigeration. PX can be recovered with propylene level refrigeration if it's starting concentration is high enough the PX can be frozen out of the solution at the level of refrigeration achievable with propylene. If the PX is not concentrated enough, then lower temperature (ethylene level refrigeration) is required to crystallize the PX out of the solution. Using only propylene level refrigeration will reduce equipment and energy requirements.

Figure 5:
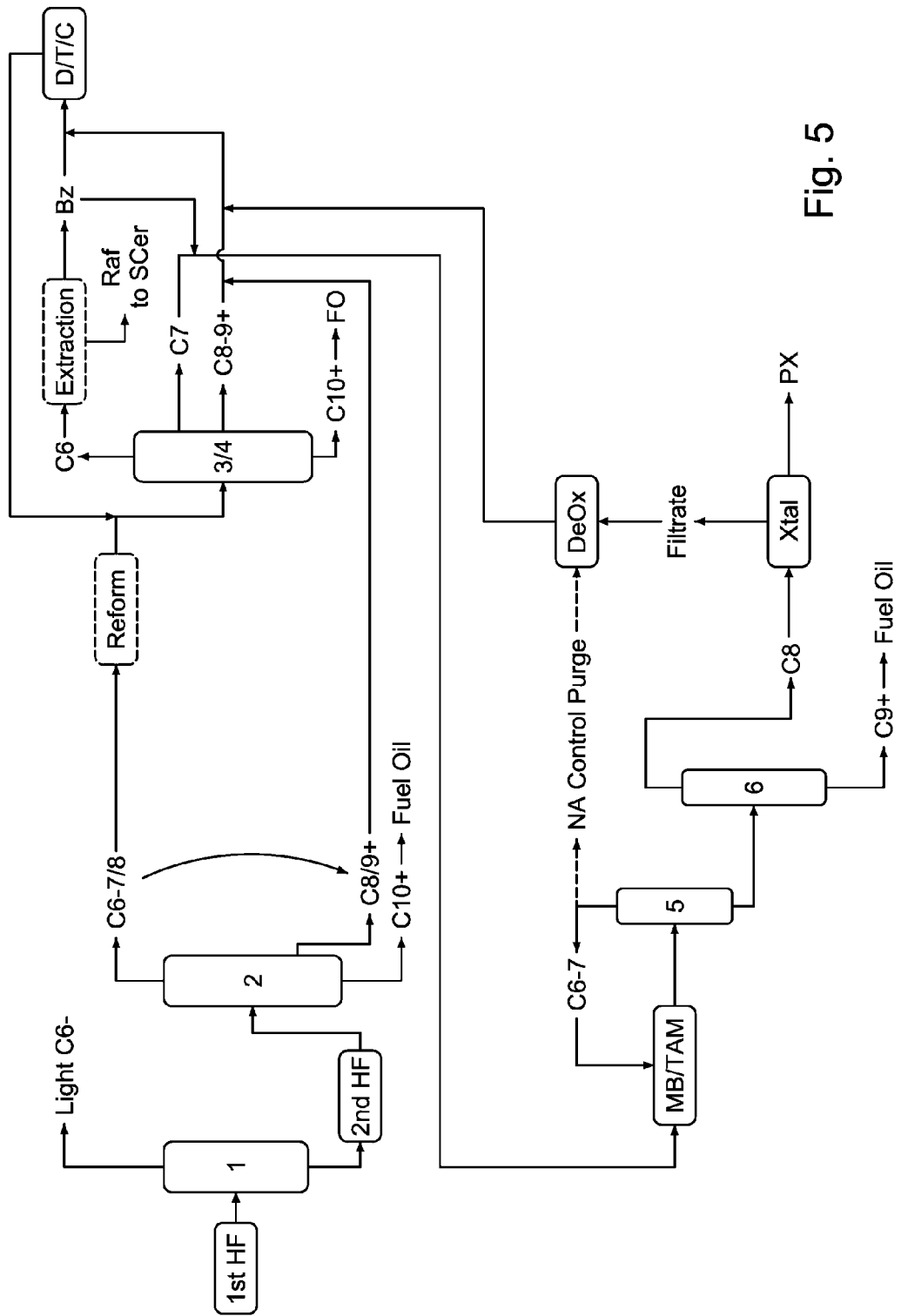

FIG. 5 illustrates yet still another embodiment of the invention, similar to the embodiment shown in FIG. 3, with the exception of the operation of fractionators 2 and 3/4. In the process shown by FIG. 5, fractionator 2 is operated so that most of the C8 species are sent, along with C9+ species, to be merged with the C8 and C9+ fraction from the one or more fractionators illustrated by fractionator 3/4.

Figure 6:
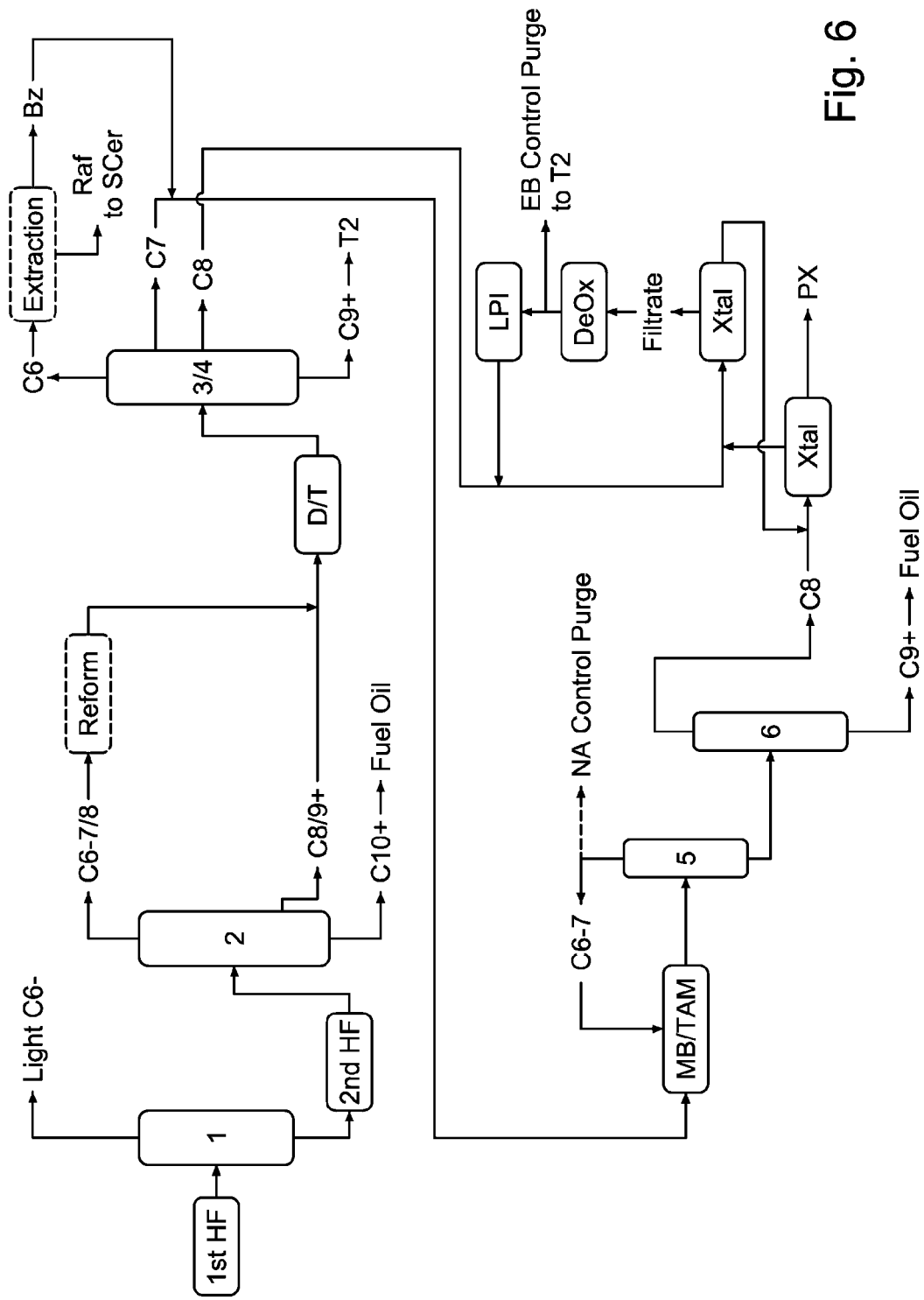

FIG. 6 illustrates yet again another embodiment of the present invention. This embodiment differs from earlier embodiments principally in that the overhead from fractionator 2, after passing through the reformer, is merged with a C8/C9+ cut from said fractionator and sent to a reactor where the material is subjected to dealkylation and/or transalkylation ("D/T") to increase the benzene and/or toluene content thereof. The product of the D/T reactor is then processed in a similar manner as in the earlier embodiments. FIG. 6 also shows recovery of equilibrium xylenes obtained from the one or two fractionator(s) 3/4. The C8 stream is processed in a two stage crystallizer (with ethylene level refrigeration now required), as shown in the figure, including merging with the xylenes obtained from the alkylation reactor (MB/TAM). As shown in the figure, the crystallizer filtrate is deoxygenated ("DeOx") and then subjected to liquid phase isomerization in a process per se known in the art. Vapor phase isomerization can also be used in this step. A purge may be required to prevent accumulation of EB (ethyl benzene), which can be routed to fractionator 2 (T2). The two stage crystallizer can be operated using ethylene-level refrigeration.

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process comprising:
   (a) treating a first hydrocarbon stream from a reformer in a steam cracker under suitable conditions to produce a second stream comprising C6-C10+ aromatic hydrocarbons, then
   (b) dealkylation and/or transalkylation and/or cracking (D/T/C) of at least a portion of said second stream by contact with a suitable catalyst under suitable reaction conditions to produce a third stream having an increased benzene and/or toluene content compared with said second stream and a light paraffin by-product; then
   (c) methylating at least a portion of said third stream with a methylating agent to selectively produce para-xylene and optionally a light olefin and/or light paraffin by-product; and then
   (d) a step of recovering para-xylene;
   wherein said first hydrocarbon stream, prior to step (a), and/or said second stream, prior to step (b), undergo at least one process prior to steps (b) or (c), respectively, said at least one other process selected from: (a) an isomerization process to convert ethylbenzene to xylenes; (b) a hydrotreating process to remove a portion or all of the di-olefins and/or a portion or all of the mono-olefins; (c) an extraction process to remove non-aromatic hydrocarbons; (d) a de-hexane process where C6 paraffins are separated from the C6 naphthenes and benzene; (e) a de-benzene process to remove at least a portion of the benzene in the feedstock, optionally then recovered and/or recycled; (f) fractionation to remove toluene prior to the dealkylation/transalkylation/cracking reactor.

2. The process of claim 1, wherein step (d) comprises the use of a crystallizer.

3. The process of claim 1, wherein step (d) comprises the use of an adsorptive separation unit.

4. The process according to claim 1, wherein said methylating agent is methanol.

5. The process of claim 1, including at least one step of removing oxygen-containing impurities from a process stream in said process.

* * * * *